United States Patent [19]

Fridinger

[11] 4,013,444
[45] Mar. 22, 1977

[54] INHIBITING GRASS GROWTH WITH 5-ACETAMIDO-2,4-DIMETHYLTRI-FLUOROMETHANESULFONANILIDE

[75] Inventor: Tomas L. Fridinger, Woodbury, Minn.

[73] Assignee: Minnesota Mining and Manufacturing Company, St. Paul, Minn.

[22] Filed: June 19, 1975

[21] Appl. No.: 588,393

Related U.S. Application Data

[62] Division of Ser. No. 331,676, Feb. 12, 1973, Pat. No. 3,894,078.

[52] U.S. Cl. ........................................ 71/76; 71/103
[51] Int. Cl.² ............................................ A01N 9/14
[58] Field of Search ................................ 71/103, 76

[56] References Cited

UNITED STATES PATENTS

| | | | |
|---|---|---|---|
| 3,639,474 | 2/1972 | Harrington | 71/103 X |
| 3,661,552 | 5/1972 | Rumanowski | 71/118 |
| 3,888,654 | 6/1975 | Abramitis | 71/118 X |

Primary Examiner—Lewis Gotts
Assistant Examiner—Catherine L. Mills
Attorney, Agent, or Firm—Cruzan Alexander; Donald M. Sell; Donald C. Gipple

[57] ABSTRACT

5-Acetamido-2,4-dimethyltrifluoromethanesulfonanilide. This compound is a plant growth regulator.

2 Claims, No Drawings

INHIBITING GRASS GROWTH WITH 5-ACETAMIDO-2,4-DIMETHYLTRIFLUOROMETHANESULFONANILIDE

This is a division of application Ser. No. 331,676, now U.S. Pat. No. 3,894,078, with which this application was copending.

This invention relates to 5-acetamido-2,4-dimethyltrifluoromethanesulfonanilide. This compound is a plant growth regulator.

BACKGROUND OF THE INVENTION

N-substituted perfluoroalkanesulfonamides are broadly described in U.S. Pat. No. 3,639,474 as active herbicides and plant growth modifiers. 5-Acetamido-2methyltrifluoromethanesulfonanilide and 5-acetamido-2-chlorotrifluoromethanesulfonanilide were particularly disclosed therein to have particular plant growth modifying activity, i.e. as to their ability to retard the growth of grass without significant distortion of the normal foliar shape. This plant growth modifying activity is of interest because it reduces the number of times grass must be mowed.

It has now been found that a novel derivative of trifluoromethanesulfonanilide, 5-acetamido-2,4-dimethyltrifluoromethanesulfonanilide, is a much more effective grass growth regulator than 5-acetamido-2-methyltrifluoromethanesulfonanilide, the preferred compound of the above mentioned patent. It has been found, both in greenhouse testing and in outdoor testing, that the compounds of the present invention can be used at greatly reduced rates of application. This result is both unexpected and economically desirable.

The invention also includes horticulturally acceptable salts of 5-acetamido-2,4-dimethyltrifluoromethanesulfonanilide, novel intermediates useful for its preparation and processes for the preparation thereof.

DETAILED DESCRIPTION OF THE INVENTION

This invention relates to the compound 5-acetamido-2,4-dimethyltrifluoromethanesulfonanilide

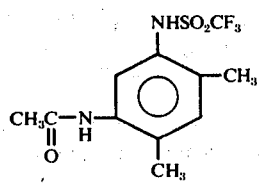

as well as horticulturally acceptable salts thereof, certain intermediates therefor and processes for the preparation thereof. The compound is useful as a herbicide and plant growth modifier.

It is therefore an object of the invention to provide the compound 5-acetamido-2,4-dimethyltrifluoromethanesulfonanilide and its horticulturally acceptable salts.

It is another object of the invention to provide the compound 5-amino-2,4-dimethyltrilfluoromethanesulfonanilide.

It is another object of the invention to provide the compound 5-nitro-2,4-dimethyltrifluoromethanesulfonanilide.

It is another object of the invention to provide the compound 2,4-dimethyltrifluoromethanesulfonanilide.

It is another object of the invention to provide a process for the preparation of 5-acetamido-2,4-dimethyltrifluoromethanesulfonanilide by reacting trifluoromethanesulfonylfluoride, chloride or anhydride with 5-amino-2,4-dimethylacetanilide.

It is another object of the invention to provide a process for the preparation of 5-acetamido-2,4-dimethyltrifluoromethanesulfonanilide by reacting acetic anhydride or acetyl chloride with 5-amino-2,4-dimethyltrifluoromethanesulfonanilide.

The salts of the invention are prepared by treating the acid form compound (shown in the foregoing Formula I) with a stoichiometrically equivalent amount of an appropriate base under mild conditions. Among the metal salts of the invention are alkali metal (e.g. lithium, sodium and potassium), alkaline earth metal (e.g. barium, calcium and magnesium) and heavy metal (e.g. zinc and iron) salts as well as other metal salts such as aluminum. Appropriate bases for use in preparing the metal salts include metal oxides, hydroxides, carbonates, bicarbonates and alkoxides. Some salts are also prepared by transmetallation reactions. The organic amine salts include the salts of alkylamines and aromatic amines, preferably containing not more than ten carbon atoms. These and the ammonium salts can be prepared by reacting the acid form with the appropriate organic base or ammonium hydroxide. The salts of the invention are frequently formed by reacting the precursors in aqueous solution. This solution can be evaporated to obtain the salt of the compound as a dry powder. In some cases, it may be more convenient to use a nonaqueous solvent such as alcohols, acetone, etc. Since many of the salts are water soluble, they are often used in the form of aqueous solutions.

The compound of the present invention is quite active as a preemergence herbicide at rates of application such as 20, 10 and 5 pounds per acre. It even shows interesting activity at 2.5 pounds per acre. Good control of nutsedge (Cyperus sp.) is obtained by preemergence application of 2.5 pounds of active ingredient per acre. When applied postemergence as a plant growth regulator, and particularly as a grass growth regulator, it shows high activity at an application rate of 2 pounds per acre and the rate applied may be as low as 0.15 pounds per acre while maintaining control of grass growth.

In order to be used as a plant growth regulator or as a herbicide, the rate of application will vary as taught hereinabove. When the compound is used at low rates it may be toxic to a few weed species, although its primary function is as a grass growth regulator. Of course, it must be safe to the grass species treated at the chosen rate of application.

Whether used as a plant growth regulator or herbicide, the compound of the invention and its salts can be used alone, for example, as dusts or granules of the compounds, or preferably they may be applied in formulations containing the active ingredients in a horticulturally acceptable extending medium including wax bars pf various types. The formulations are comprised of one or more active ingredients and one or more adjuvants and/or carriers. Specific formulations are useful to facilitate the application of the compounds and to achieve specific biological objectives such as controlling the availability of the herbicide, improving adherence to plants, and the like, as is well known to those skilled in the art.

The compounds of the invention may be formulated as wettable powders, emulsifiable concentrates, aqueous or nonaqueous solutions and/or suspensions, granules, dusts, wax bars and the like. Said compounds as such can be finely divided and dispersed or suspended in any of the usual aqueous media, or if appropriate salts are used, a solution may be made. Spreading agents, wetting agents, sticking agents or other adjuvants can be added as desired.

When emulsifiable concentrates are prepared the active ingredient can be present in concentration of about 5% to 80% or more, depending upon its solubility in water, but it has been found that the compounds of this invention are preferably used in a concentration of 20 to 50%. The units of concentration are weight per unit weight. When the active ingredients are not in salt form, they are soluble in common organic horticultural solvents such as benzene, toluene, xylene, dichloromethane, chloroform, hexane and heptane or less highly refined aromatic or aliphatic hydrocarbons and mixtures thereof. Examples of these are coal tar fractions, straight run petroleum distillates, thermolytically or catalytically cracked hydrocarbon oil, gas oil, light lubricating oil fractions, kerosene, mineral seal oil, and the like. In appropriate cases, oxygenated solvents such as ketones may be used in or as the carriers. These concentrates can be dispersed in water to permit the use of an aqueous spray. Admixture with a small amount of an organic surface active agent capable of lowering the surface tension of water is preferred, so as to produce more or less stable emulsions.

Examples of surface active agents variously known as dispersing agents, wetting agents or emulsifying agents comprise soft or hard soaps, morpholine or dimethylamine oleate, sulfonated fish, castor and petroleum oils, sodium salts of lignin sulfonic acid, alkylated aromatic sodium sulfonates, such as decylbenzene sodium sulfonate, dodecylbenzene sodium sulfonate, butyl or other amine salts of decyl or dodecylbenzene sulfonic acid, sodium lauryl sulfate, disodium monolauryl phosphate, ethylene oxide condensation products of higher alcohols or higher mercaptans. Mixtures of two or more surface active agents are also feasible. Generally, the surface active agent will comprise only a small proportion of the composition, e.g. 0.1–15% by weight of the toxicant.

The formulation of dry compositions for application as granules, dusts or for further dilution with liquid carriers is readily accomplished by mixing the active compound with a solid carrier. Such solid carriers will be of various sizes from dust to granules. The techniques for such formulations are well known to the art. Suitable carriers include charcoal, talc, clay, pyrophyllite, silicas, fuller's earth, lime, diatomaceous earth, flours (such as walnut shell, wheat, soya bean, cottonseed and wood flours), magnesium and calcium carbonate, calcium phosphate and the like. Powders may be granulated by the use of suitable binders such as cellulose derivatives, for example ethyl or carboxymethyl, corn syrup, and the like. The compounds of the above formulations are applied by spraying, spreading, dusting or the like.

The rate of application will of course vary, but the compound of the invention exhibits satisfactory preemergence control of broadleaf and grass weeds at the application rate of about 2 to 20 pounds per acre. As a plant growth regulator, and particularly as a grass growth regulator, activity is obtained at rates as low as one-eighth pound per acre on growing plants. The maximum rate depends upon the sensitivity of the growing plant. For reasons of economy the lowest effective rate is chosen, and for most grasses this will be less than one pound per acre. Local conditions, for example temperature, humidity, wind, precipitation, nature of the soil and the like may require greater or smaller amounts. Effective resolution of these factors is within the skill of those versed in the agricultural art.

The compositions set out hereinabove may contain, in addition to the compounds of the invention, other biologically active substances. Thus, insecticides and fungicides may be incorporated in the compositions. Further, if desired, the compositions may contain fertilizers, trace metals or the like and when applied directly to the soil may additionally contain nematicides, soil conditioners, plant regulators and/or herbicides of similar or different properties.

The compound of the invention is broadly active as a preemergence herbicide. In addition it also shows various types of plant growth modifying activity. Plant growth modification as defined herein consists of all deviations from natural development, for example, defoliation, stimulation, stunting, retardation, desiccation, tillering, dwarfing, regulation and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants. It has been found that herbicidal activity can be separated from certain other plant growth modifying activity by controlling the rate and the method of application. Of particular interest is the ability to slow the rate of growth of grass.

The compound of the invention is readily prepared by the two following methods, A and B.

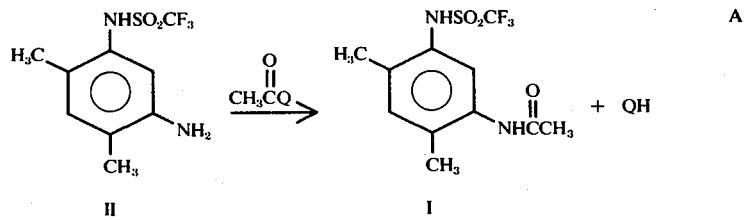

wherein Q is halogen, preferably chlorine or the anhydride residue

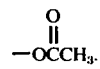

Acetic anhydride is preferred because it is inexpensive and easy to use. The reaction may be carried out in suitable non-reactive solvents such as esters of organic acids (e.g. ethyl acetate), amides of organic acids (e.g. N,N-dimethylformamide), ethers (e.g. tetrahydrofuran), chlorinated hydrocarbons (e.g. ethylenedichloride), and the like. It can also be carried out in the absence of solvent.

The reaction temperature may be from about 0° C. to 100° C., depending upon the rate of reaction desired. The reaction proceeds readily at room temperature (about 25° C.).

The second method, B, is illustrated by the following equation

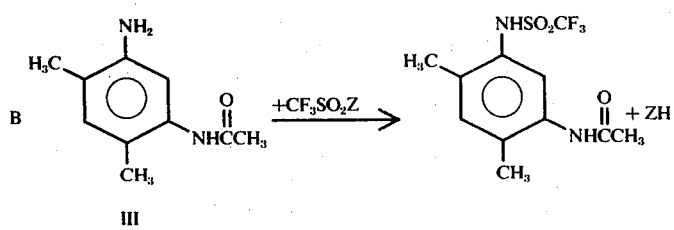

wherein Z us fluorine, chlorine or the trifluoromethanesulfonate residue $—OSO_2CF_3$, and preferably it is fluorine. It is preferred to use an acid acceptor such as an organic base.

A solution of the primary arylamine and a substantially equimolar quantity of acid acceptor (such as triethylamine, dimethylaniline, pyridine and the like) in an inert organic solvent is ordinarily used. However, an acid acceptor is not always necessary, and an excess of the primary arylamine may also serve as acid acceptor. Among the suitable solvents are 1,2-dimethoxyethane, ethyl acetate, benzene, chloroform, dichloromethane, dimethylacetamide, dimethylformamide and the like. Alternatively an excess of the primary arylamine may be used or the reaction may be carried out in the absence of solvent. Generally, an equimolar quantity of the trifluoromethanesulfonic anhydride or chloride is added to the solution. The addition is advantageously carried out at −15° C. to 50° C. It is advantageous to allow the reaction mixture to remain at reflux temperature for a few hours following addition. The reaction of Method B may also be carried out in a high pressure reactor. This technique is particularly preferred when the sulfonyl fluoride is used as reactant. The reaction is usually carried out at temperature ranges of 0° to 150° C., but these temperatures may be raised or lowered. Presently preferred is a temperature of about 80° to 100° C. The reaction may be carried out without solvent, or with dimethylformamide, ethyl acetate or excess tertiary amine as solvent, but other advantageous variations are possible.

It will be appreciated that the scope of this invention encompasses a wide range of reaction conditions and the synthetic methods A and B discussed herein are described in general and preferred language. However, a great variation in the use of these synthetic techniques is possible, and this invention is broadly inclusive of such variation.

After completion of the reaction, the product is isolated by conventional methods. For example, the reaction mixture can be extracted with excess aqueous sodium hydroxide. The aqueous extract is then washed with organic solvents and treated with charcoal to remove impurities. Subsequent acidification of the aqueous extract with mineral acid then affords the product as a solid which is recrystallized as required to give pure product. When water-soluble solvents are used, the reaction mixture can be poured directly into aqueous mineral acids. The product is then isolated by conventional extraction techniques and purified as above.

The intermediate used in process A (II, 5-amino-2,4-dimethyltrifluoromethanesulfonanilide) is a novel compound and is part of the present invention. It can be prepared by reaction of the known compound 4,6-dimethyl-m-phenylenediamine with trifluoromethanesulfonyl fluoride. The reaction is preferably carried out in the presence of an acid acceptor (such as a tertiary amine such as trimethylamine, triethylamine or N,N-dimethylaniline) and with or without a solvent. Suitable nonreactive solvents include esters of aliphatic acids such as ethyl acetate, amides of aliphatic acids such as N,N-dimethylformamide, and the like. The temperature range used is about 40° C. to −10° C. When the reaction is carried out in the absence of solvent an excess of tertiary amine may be used.

Alternatively 5-amino-2,4-dimethylfluoromethanesulfonanilide may be prepared in three steps from 2,4-xylidine. 2,4-Xylidine is trifluoromethylsulfonylated to provide the novel compound 2,4-dimethyltrifluoromethanesulfonanilide by using the general method described hereinabove. Nitration of this intermediate provides the novel intermediate 2,4-dimethyl-5-nitrotrifluoromethanesulfonanilide. Reduction of the nitro compound provides the desired 5-amino-2,4-dimethyltrifluoromethanesulfonanilide.

2,4-Dimethyl-5-nitrotrifluoromethanesulfonanilide is also prepared by the reaction of trifluoromethanesulfonyl fluoride with 5-nitro-2,4-xylidine by using the general method described hereinabove.

The intermediate III, used in process B, is known.

The following examples are given for the purpose of further illustrating the present invention but are not intended, in any way, to be limiting on the scope thereof. All parts are by weight unless otherwise specifically noted.

EXAMPLE 1

Trimethylamine (174 g., 2.95 mole), trifluoromethanesulfonyl fluoride (129 g., 0.826 mole), ethyl acetate (175 ml.) and 5-amino-2,4-dimethylacetanilide (105 g., 0.59 mole) were heated for one day in about one liter of ten percent sodium hydroxide solution. The resulting solution was steam distilled until no basic distillate was obtained. The residual solution was cooled with an ice bath, then filtered to remove insoluble impurities. The filtrate was extracted twice with 500 ml. portions of dichloromethane. The aqueous phase was filtered, then the filtrate was cooled with an ice bath and acidified with cold dilute hydrochloric acid to provide a light yellow solid. The product was washed with water and dried to provide 155 g. (85%) of 5-acetamido-2,4-dimethyltrifluoromethanesulfonanilide, m.p. 170°–176° C. Further purification was effected by recrystallization from acetonitrile to provide product with m.p. 181°–184° C.

| Analysis: | %C | %H | %N |
|---|---|---|---|
| Calculated for: $C_{11}H_{13}F_3N_2O_3S$: | 42.6 | 4.2 | 9.0 |
| Found: | 42.4 | 4.2 | 8.9 |

An alternative work-up of the reaction mixture from the pressure reactor is to pour it into dilute hydrochloric acid, filter the crude product and dry it, or extract rather than filter, followed by drying and isolation of the product.

EXAMPLE 2

To a solution of 2,4-dimethyl-m-phenylenediamine (50 g., 0.37 mole), having the structure

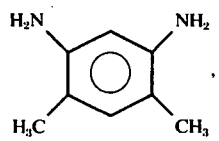

and trimethylamine (109 g., 1.85 mole) in a pressure reactor was added slowly over about twelve hours about 48 g. (0.32 mole) of trifluoromethanesulfonyl fluoride. During the addition the temperature was maintained at about 90° C., then the reaction was maintained for an additional 12 hours at 90° C. Sodium hydroxide solution (44.9 g. in about 1 liter of water) was added to the reaction mixture and the mixture was steam distilled until the distillate was neutral. The aqueous residue was washed with ethyl acetate, then acidified with concentrated hydrochloric acid. The aqueous phase was washed with dichloromethane, then treated with about 600 ml. of five percent sodium hydroxide solution. The product, 5-amino-2,4-dimethyltrifluoromethanesulfonanilide precipitates and was isolated by filtration. It was found to be relatively free from impurities by thin layer chromatography, m.p. 145°–150° C.

5-Amino-2,4-dimethyltrifluoromethanesulfonanilide (0.141 g., 0.53 mmole) was treated with excess acetic anhydride (0.5 ml.) while stirring at room temperature at about 25° C. The mixture was then evaporated to dryness under vacuum. The product, 5-acetamido-2,4-dimethyltrifluoromethanesulfonanilide, was transferred to another vessel with dichloromethane, the solvent was evaporated under vacuum and the yellow solid dried overnight at 60° C. to m.p. 180°–182° C.

EXAMPLE 3

Trimethylamine (21.2 g., 0.36 mole) trifluoromethanesulfonyl fluoride (13.8 g., 90 mmole), ethyl acetate (25 ml.) and 5-nitro-2,4-xylidine (12 g., 72 mmole) were heated for one day at about 90° C. in a pressure reactor. The reaction mixture was then treated with about 150 ml. of ten percent sodium hydroxide solution. The resulting mixture was steam distilled until no basic distillate was obtained. The residual solution was cooled in an ice bath, then filtered to remove insoluble impurities. The filtrate was acidified with cold dilute hydrochloric acid, giving a semisolid. The mixture was extracted thrice with 200 ml. portions of dichloromethane. The dichloromethane extracts were washed twice with 200 ml. portions of water, dried over anhydrous sodium sulfate and evaporated to dryness. The residue was taken up in diethyl ether (100 ml.), filtered, the ether was evaporated off and the residue was recrystallized from hexane to give 2,4-dimethyl-5-nitrotrifluoromethanesulfonanilide, m.p. 80°–82° C.

| Analysis: | %C | %H | %N |
|---|---|---|---|
| Calculated for: $C_9H_9F_3N_2O_4S$: | 36.2 | 3.0 | 9.4 |
| Found: | 36.3 | 3.1 | 9.4 |

EXAMPLE 4

The effects of postemergence application of the compound of the invention and 5-acetamido-2-methyltrifluoromethanesulfonanilide (described in U.S. Pat. No. 3,639,474) as diethanolamine salts on the growth of Kentucky bluegrass were evaluated. Plants were trimmed to a uniform two inch height and sprayed to runoff with solutions of various concentrations of the compounds in water. The control was sprayed with water alone.

The test solutions were prepared by mixing approximately equimolar proportions of the acid form compound and diethanolamine in water, thus forming the diethanolamine salt in situ. The results were as follows:

| Compound | Solution Concentrations, parts per million | | | | | | |
|---|---|---|---|---|---|---|---|
| | 2000 | 500 | 250 | 125 | 62.5 | 31.25 | 15.63 |
| 5-acetamido-2,4-dimethy-trifluoromethanesulfon-anilide diethanolamine salt | E | E | C | B | A | A | A |
| 5-acetamido-2-methyltri-fluoromethanesulfonanilide diethanolamine salt | B | B | A | A | A | A | A |
| Control | 1. | 1. | 1. | 1. | 1. | 1. | 1. |

1. = normal stand, no injury
A. equal to the control
B. slight to ¼ inhibition of growth
C. moderate - ¼ to ½ inhibition of growth
D. ½ to ¾ inhibition of growth
E. ¾ to complete inhibition This test shows that the compound of the invention at a rate of 125 ppm is equal to 5-acetamido-2-methyltrifluoromethanesulfonanilide at rates of 500 and 2000 ppm. The compound of the invention shows maximum activity at 500 ppm, whereas 5-acetamido-2-methyltrifluoromethanesulfonanilide does not show maximum activity at 2000 ppm. Thus, the compound of the invention is 4 to 8 or more times as active as 5-acetamido-2-methyltrifluoromethanesulfonanilide in this test.

EXAMPLE 5

The effects of postemergence application of plant growth regulators on the growth of Merion Kentucky bluegrass were evaluated as follows. The grass was trimmed to a uniform two inch height and sprayed to runoff with solutions of compound in water. An untreated check was maintained. After sixty days twelve square feet of each plot replication were mowed. Collected clippings were allowed to dry to a constant weight.

| | Treatment | Rate (lb. per acre) | Mean Weight of Clippings From 4 Replications (in g.) |
|---|---|---|---|
| A) | 5-acetamido-2-methyltrifluoromethanesulfonanilide diethanolamine salt | 4.0 | 113.4 |
| B) | 5-acetamido-2,4-dimethyltrifluoromethanesulfonanilide diethanolamine salt | 2.0 | 47.9 |
| | 5-acetamido-2,4-dimethyltrifluoromethanesulfonanilide diethanolamine salt | 1.0 | 58.7 |
| | 5-acetamido-2,4-dimethyltrifluoromethanesulfonanilide diethanolamine salt | 0.5 | 65.5 |
| | 5-acetamido-2,4-dimethyltrifluoromethanesulfonanilide diethanolamine salt | 0.25 | 106.7 |
| | Untreated check | | 239.7 |

This test demonstrates that the compound of the invention provides activity at 0.25 lbs. per acre equal or better than the activity of compound A) at 4.0 lbs. per acre.

What is claimed is:

1. The method for inhibiting the rate of the growth of grass which comprises contacting grass with an effective amount of 5-acetamido-2,4-dimethyltrifluoromethanesulfonanilide or a horticulturally acceptable salt thereof.

2. The method according to claim 1 for inhibiting the growth of grass which comprises contacting grass with an effective amount, less than one pound per acre and as low as one-eighth pound per acre of 5-acetamido-2,4-dimethyltrifluoromethanesulfonanilide or a horticulturally acceptable salt thereof.

* * * * *